(12) United States Patent
Siccardo

(10) Patent No.: US 9,974,876 B2
(45) Date of Patent: May 22, 2018

(54) METHOD AND DEVICE FOR DISINFECTING SPACES AND SURFACES

(71) Applicant: 99 HOLDING S.A.R.L., Luxembourg (LU)

(72) Inventor: Giovanni Siccardo, Bergamo (IT)

(73) Assignee: 99 HOLDING S.A.R.L., Luxembourg (LU)

( * ) Notice: Subject to any disclaimer, the term of this patent is extended or adjusted under 35 U.S.C. 154(b) by 127 days.

(21) Appl. No.: 14/784,519

(22) PCT Filed: Apr. 16, 2014

(86) PCT No.: PCT/IB2014/060772
§ 371 (c)(1),
(2) Date: Oct. 14, 2015

(87) PCT Pub. No.: WO2014/177966
PCT Pub. Date: Nov. 6, 2014

(65) Prior Publication Data
US 2016/0067364 A1    Mar. 10, 2016

(30) Foreign Application Priority Data

May 2, 2013   (IT) ............................... BO2013A0192

(51) Int. Cl.
*A61L 2/22* (2006.01)
*A61L 2/24* (2006.01)
(Continued)

(52) U.S. Cl.
CPC .................. *A61L 2/22* (2013.01); *A61L 2/24* (2013.01); *A61L 2/28* (2013.01); *A61L 9/14* (2013.01);
(Continued)

(58) Field of Classification Search
CPC ...................................... A61L 2/22; A61L 2/24
(Continued)

(56) References Cited

U.S. PATENT DOCUMENTS

2011/0247655 A1* 10/2011 Lewis ...................... A23B 7/10
134/18
2012/0275953 A1* 11/2012 Lukasik ................. A61L 2/208
422/28
(Continued)

FOREIGN PATENT DOCUMENTS

GB          2469018 A      10/2010
WO     WO2012033850 A2    3/2012

OTHER PUBLICATIONS

International Search Report and Written Opinion dated Dec. 17, 2014 for related PCT Application No. PCT/IB2014/060772.

*Primary Examiner* — Kevin Joyner
(74) *Attorney, Agent, or Firm* — Shuttleworth & Ingersoll, PLC; Timothy J. Klima

(57) ABSTRACT

A system for the disinfection of rooms and surfaces including at least one plate which can be associated with a room to be treated and equipped with a memory containing a plurality of identification data of the room and at least one diffuser device including a tank containing a liquid solution and nebulising means associated with the tank and designed to draw out the liquid solution from the tank spraying it in the space. The diffuser device includes a control unit associated with the nebulising means and which can be associated with the plate, designed for receiving from the plate a signal representing identification data of the room and designed for controlling the nebulising means as a function of the signal in such a way as to sanitise the room in an automatic manner.

24 Claims, 4 Drawing Sheets

(51) Int. Cl.
*A61L 2/28* (2006.01)
*A61L 9/14* (2006.01)
*B05B 12/00* (2018.01)

(52) U.S. Cl.
CPC ......... *B05B 12/004* (2013.01); *A61L 2202/14* (2013.01); *A61L 2202/25* (2013.01); *A61L 2209/11* (2013.01); *G16H 40/20* (2018.01)

(58) Field of Classification Search
USPC .............................................. 239/302; 422/28
See application file for complete search history.

(56) References Cited

U.S. PATENT DOCUMENTS

| | | | | |
|---|---|---|---|---|
| 2013/0183749 A1* | 7/2013 | Aamodt | .................... | A61L 9/14 435/287.1 |
| 2013/0302208 A1* | 11/2013 | Hill | ......................... | A61L 2/24 422/3 |

\* cited by examiner

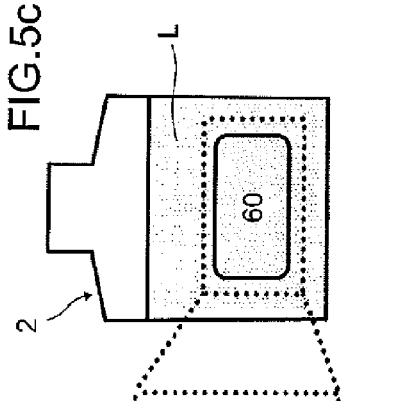
FIG.5a
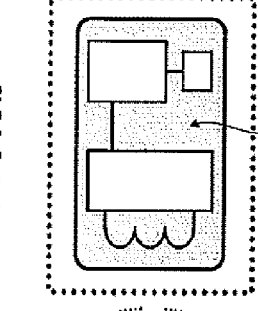
FIG.5b
FIG.5c
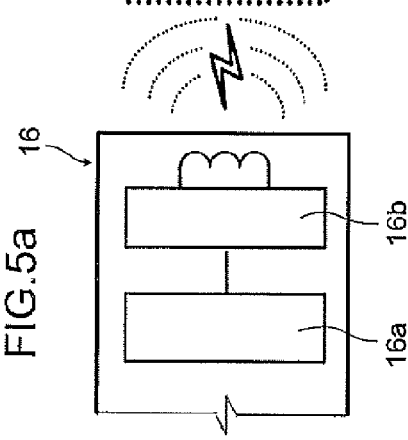
FIG.6

METHOD AND DEVICE FOR DISINFECTING SPACES AND SURFACES

This application is the National Phase of International Application PCT/IB2014/060772 filed Apr. 16, 2014 which designated the U.S. and that International Application was published under PCT Article 21(2) in English.

This application claims priority to Italian Patent Application No. BO2013A000192 filed May 2, 2013, which application is incorporated by reference herein.

TECHNICAL FIELD

This invention relates to a diffuser device, system and method for the disinfection of spaces and surfaces.

BACKGROUND ART

The invention applies in particular to the disinfection of rooms and the surfaces contained therein, by the nebulising and diffusion of disinfectant solutions.

One of the age-old problems affecting public structures has always been that linked to the risk of their visitors catching infections. Amongst the public area that potentially suffer from this problem we can list, amongst others: schools, public offices, hotels, restaurants, trains, aircraft and hospitals, the latter of particular interest given the high number of users and their particular state of health.

In the hospital context it is possible to identify at least two types of patients/operators:
  in-patients, possibly "run-down" (immunosupressed, the elderly with multiple pathologies, premature babies, malnourished individuals), the organisms of whom do not have the capacity to respond adequately to bacterial attacks;
  patients who undergo surgery, for whom it has been demonstrated that 10 CFU/m3 is sufficient to cause a serious arthropathy, where CFU/m3 is the unit of measurement of the volumetric "colony-forming unit (CFU)", that is, the concentration of the CFUs per unit of volume, whilst CFU/m2 is the unit of measurement of the surface CFU.

In light of this, the prior art proposes disinfectant solutions which are able to instantaneously attack all the organic substances with which they enter into contact, destroying viruses, bacteria, spores, fungi and biofilm present in the air and on the surfaces.

These disinfectant solutions can be diffused in the room by devices which are able to transform them from the liquid state to that of dry steam which, after having disinfected the air, deposits on all the surfaces, attacking the micro-organisms present.

Although the effectiveness of the diffuser systems has been widely demonstrated, and have the advantage of a potential repetition of the treatment and, consequently, the results of the disinfection, the repetition is, however, guaranteed by the capacity of the diffuser system to perform a correct disinfection, and certify that it has been performed, in a given environment. More specifically, to guarantee and certify that
  the desired room has been sanitised;
  the specified sanitising solution has been used;
  the solution has been dispensed in a continuous manner during the entire dispensing;
  the planned quantity of solution has been dispensed.

In effect, the systems for the disinfection of spaces and surfaces which are currently available on the market typically consist of a single diffuser device (or nebuliser), which can be programmed for use and be programmed by an operator for an operation of predetermined duration, which does not allow the correctness of the sanitisation treatment of a specific room to be guaranteed and certified.

DISCLOSURE OF THE INVENTION

The aim of this invention is to provide a diffuser device, system and method for the disinfection of spaces and surfaces which can overcome the above-mentioned drawbacks of the prior art.

More specifically, the aim of this invention is to provide a diffuser device and a system for the disinfection of spaces and surfaces which can guarantee the correct and complete sanitisation of the room.

Moreover, the aim of this invention is to provide an automatic and safe device and system for the disinfection of spaces and surfaces, which guarantees and certifies the accuracy of the disinfection.

These aims are achieved by a diffuser device and by a system for the disinfection of spaces and surfaces having features as disclosed herein, as well as a method for the disinfection of spaces and surfaces having features as disclosed herein.

More specifically, these aims are achieved by a diffuser device for a system for the disinfection of spaces and surfaces equipped with a plate containing a plurality of identification data of a room to be treated, the device comprising a tank containing a liquid solution, nebulising means associated with the tank and designed to draw out the liquid solution from the tank spraying it in the space. According to the invention, the diffuser device comprises a control unit associated with the nebulising means and which can be associated with the above-mentioned plate, designed for receiving from the plate a signal representing identification data of the room and designed for controlling the nebulising means as a function of the signal in such a way as to sanitise the room in an automatic manner.

More specifically, the control unit is programmed for communicating with the plate continuously during the nebulising, that is, during the treatment, so as to guarantee that the diffuser system is not moved to another room whilst the sanitising process is in progress.

Advantageously, in this way, a connection is created between the plate, and thus the room to be processed, and the device which guarantees a correct dispensing of the liquid solution, both in terms of quantity and duration.

Moreover, the device also comprises sensors means, associated with the tank and the control unit. The sensor means are designed to detect a quantity correlated with the quantity of liquid solution dispensed by the nebulising means (that is to say, the consumption of liquid solution) and to send a signal representing the quantity to the control unit.

Advantageously, the control unit is configured for calculating a threshold value of the quantity of liquid solution to be dispensed as a function of the signal representing the identification data of the room received from the plate, for comparing the threshold value with the quantity of liquid solution dispensed and for interrupting the nebulising by the nebulising means when the quantity of liquid solution dispensed exceeds the threshold value.

In this way, the correct sanitising of the room is guaranteed, as there is not merely an open loop control, but also a closed loop control, with feedback of information relative to the consumption of liquid solution and a target fixed not arbitrarily on the basis of the experience of the operator but unequivocally as a function of the data contained in the plate.

It should be noted that, preferably, the device is also equipped with recognition means which can be associated with the tank and configured for identifying the liquid solution contained in the tank. Advantageously, this prevents the device from spraying into the room a falsified substance or a substance different from that specified for the sanitising.

Preferably, the recognition means comprise a reading unit which can be associated with a label applied to the tank for reading one or more identification data of the liquid solution contained in the label.

Even more preferably, the reading unit also comprises a writing module configured for modifying the identification data of the liquid solution as a function of its consumption, actually updating the information at each nebulising, that is, at the end of each treatment/nebulising or (periodically) during the treatment/nebulising.

Moreover, it should be noted that both the plate and the diffuser device are equipped with respective memories (not volatile) programmable and accessible by a suitable device.

The memory of the diffuser device is designed for receiving from the control unit, periodically, during and/or at the end of each nebulising, a plurality of data correlated with:
 the room treated and/or
 the quantity of nebulised liquid solution and/or
 the quantity of liquid solution remaining in the tank and/or
 the date and time of nebulising and/or
 the duration of the nebulising.

Similarly, the memory of the plate is also configured to receive (and store), periodically, during and/or at the end of each nebulising, a plurality of data correlated with the quantity of nebulised liquid solution and/or the quantity of liquid solution remaining in the tank and/or the date and time of the nebulising and/or the duration of the nebulising and/or a serial number of the diffuser device used or in use.

Advantageously, this guarantees the traceability (continuously) of the treatments, from both the point of view of the diffuser device, to guarantee the recording of the traceability data, and the plate, allowing an in-situ control of the sanitisation performed.

In other words, an operator will always be able to check which treatments the nebulising device has performed and in which rooms; moreover, the same operator can monitor the number of treatments and the times they occurred in a specific room, that is, for each plate.

BRIEF DESCRIPTION OF THE DRAWINGS

These features of the invention will become more apparent from the following detailed description of a preferred, non-limiting embodiment of it, illustrated by way of example in the accompanying drawings, in which:

FIGS. 5a, 5b and 5c show a schematic and functional view of the means for identifying the liquid solution inside the tank;

FIG. 6 shows a series of curves of the function Vout=Vout (Weight), produced by a weight sensor operating on the tank.

DETAILED DESCRIPTION OF THE PREFERRED EMBODIMENTS OF THE INVENTION

Figure 1:
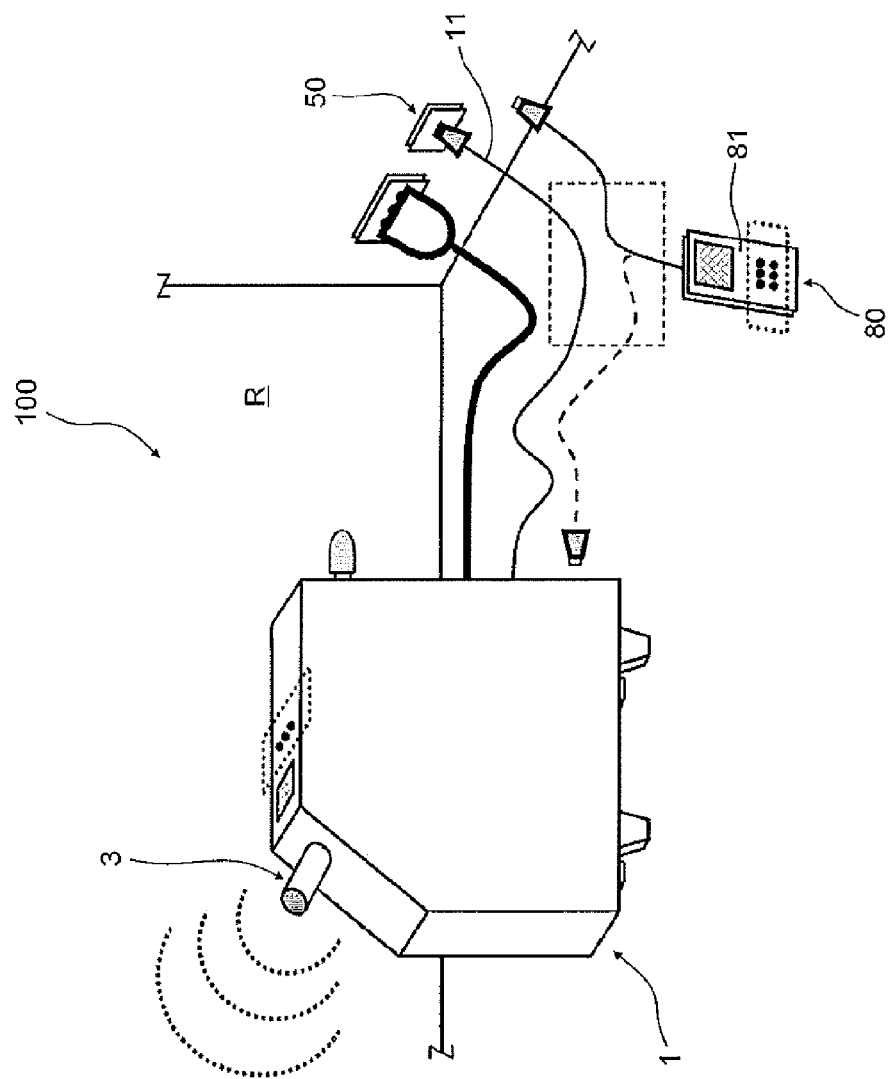
FIG. 1 shows an assembly view of the preferred implementation of the system for disinfecting spaces and surfaces according to this invention.
Figure 2:
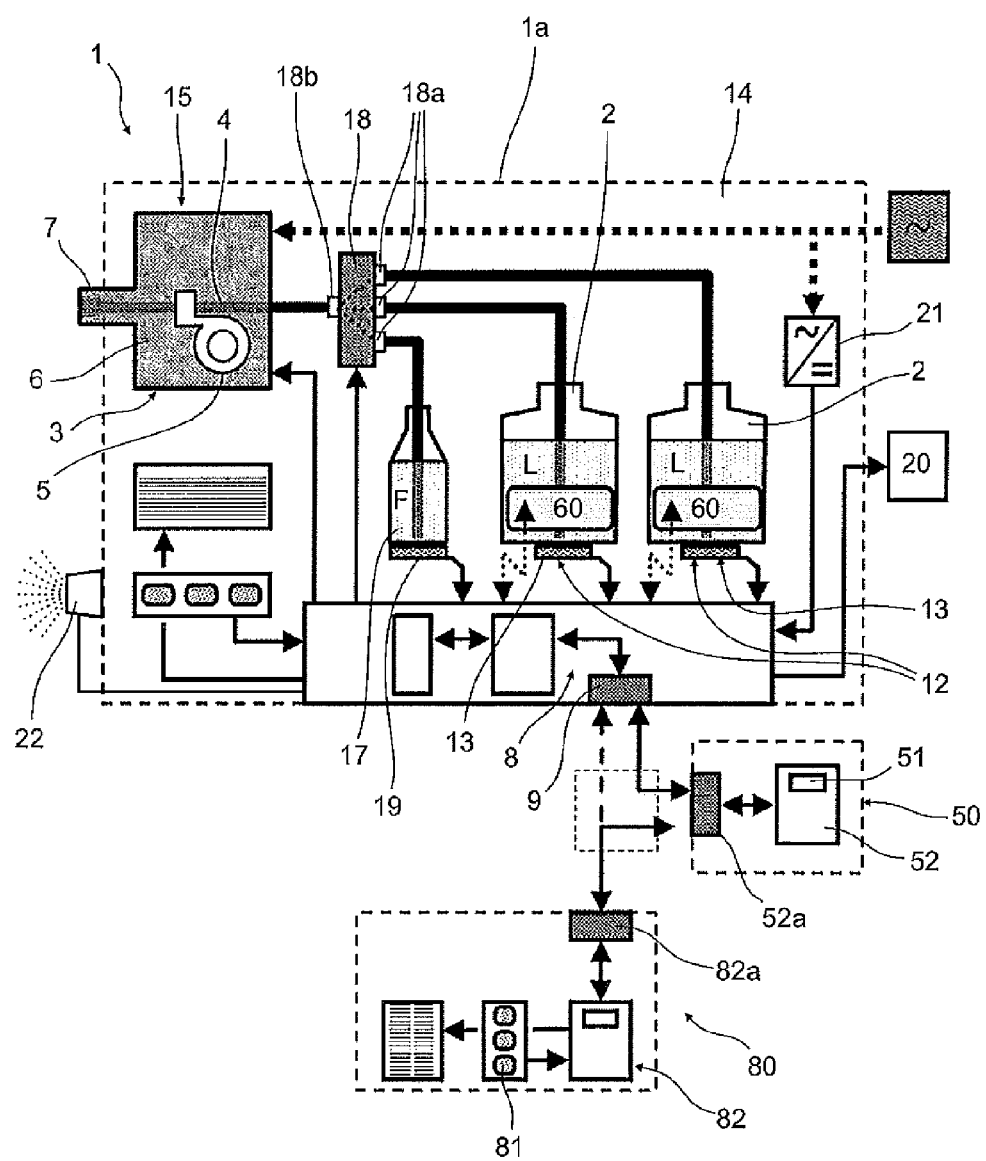
FIG. 2 shows a schematic and functional view of the system of FIG. 1.

With reference to the accompanying drawings, the numeral 1 denotes a diffuser device for a system 100 for the disinfection of spaces and surfaces according to this invention.

The diffuser device 1 is, as mentioned, inserted inside a system 100 for the disinfection of spaces and surfaces comprising at least one plate 50 containing a plurality of identification data of a room "R" to be treated.

More specifically, the plate 50 is equipped with a memory 51 containing a plurality of identification data of the room "R". The term "identification data" is used to comprise one or more of the following data:
 property;
 building and floor;
 room number;
 cubic volume;
 purpose.

Preferably, the plate 50 comprises a processor 52 associated with the memory 51 and programmable by an operator for entering the identification data of the "R".

Even more preferably, the processor 52 is equipped with a transmission module 52a connectable to the diffuser device 1 for sending to it the identification data of the room "R" to be treated.

Thus, the plate 50 comprises a processor 52 (more specifically a micro-controller), a memory 51 (of non-volatile type) and a transmission module 52a equipped with an interface circuit towards a two-way communication channel with the diffuser device 1.

The diffuser device 1 comprises a tank 2 containing a liquid solution "L" and nebulising means 3, associated with the tank 2 and designed to draw out the liquid solution "L" from the tank 2 spraying it in the space.

Preferably, the nebulising means 3 comprises a turbine 4 connected to the tank 2 through an infeed pipe from which it receives, using a pump 5, the liquid solution "L" to be nebulised.

Downstream of the turbine 4 there is also a Venturi effect (or "cross flow") pneumatic nebuliser 6, which is in fluid connection with the turbine 4 to receive a flow of air at high pressure which flows around the infeed capillary tube of the liquid. At the outfeed of the capillary tube the liquid solution "L" entering is transformed into aerosol by the air and then diffused into the space by a disperser 7. Other types of nebulisers, different from those described in the preferred embodiment, may be considered.

According to this invention, the diffuser device 1 comprises a control unit 8 associated with the nebulising means 3 and which can be associated with the plate 50. Preferably, the control unit 8 comprises at least one microprocessor 8a.

The control unit 8 is set up to receive from the plate 50 (and in particular from the transmission module 52a) a signal representing identification data of the room "R" and configured for controlling the nebulising means 3 as a function of that signal, so as to a sanitise the room in an automatic manner.

Thus, the control unit 8 comprises a data reception module 9 connectable to the plate 50, that is, to the transmission module 52a, for receiving the signal representing the identification data of the room "R".

More specifically, the control unit 8 is programmed to communicate with the plate 50 continuously during the nebulising, that is, during the treatment. In other words, the control unit 8 is designed to interrupt the nebulising (that is, to command the stopping of the nebulising means 3) following a communication failure between the data reception module 9 and the plate 50 so as to guarantee that the diffuser system is not moved to another room whilst the sanitising process is in progress.

Advantageously, this makes it possible to guarantee that the diffuser device 1 is not removed from the room whilst the treatment is in progress.

More in detail, the data reception module 9 and the transmission module 52a define a communication channel (two-way) between the diffuser device 1 and the plate 50.

The two-way communication channel allows the diffuser device 1 to communicate (during the entire treatment) with the plate 50 when the two reception 9 and transmission 52a modules are connected (that is, in communication with each other).

Figure 4:
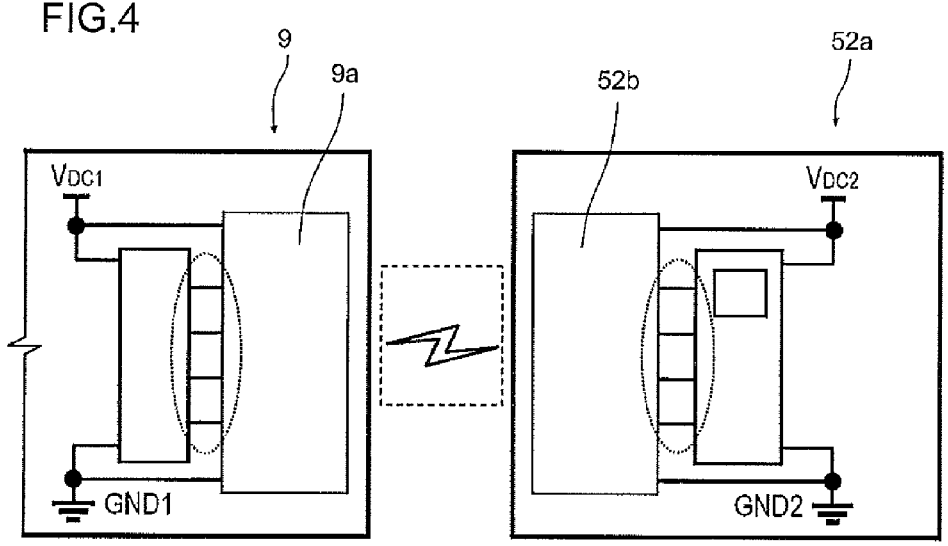
FIG. 4 shows a second embodiment of the communication channel between the diffuser device and the plate.

In a first embodiment (FIG. 4) the communication channel is a wireless bus, such as Bluetooth or Bluetooth Low Energy (BLE).

Thus, the data reception module 9 of the control unit 8 of the diffuser device 1, communicates with the transmission module 52a of the processor 52 of the electronic plate 50 by wireless communication.

From the physical point of view, the two data reception 9 and transmission 52a modules are defined by Bluetooth interface modules 9a, 52b.

It should be noted that the control unit 8 and the processor 52 interface with the corresponding data reception 9 and transmission 52a modules using a plurality of status and control signals.

The adoption of other wireless, or short range, communication technology, such as, for example, CIR (Consumer Infra Red) may be assessed and, possibly, adopted.

Figure 3:
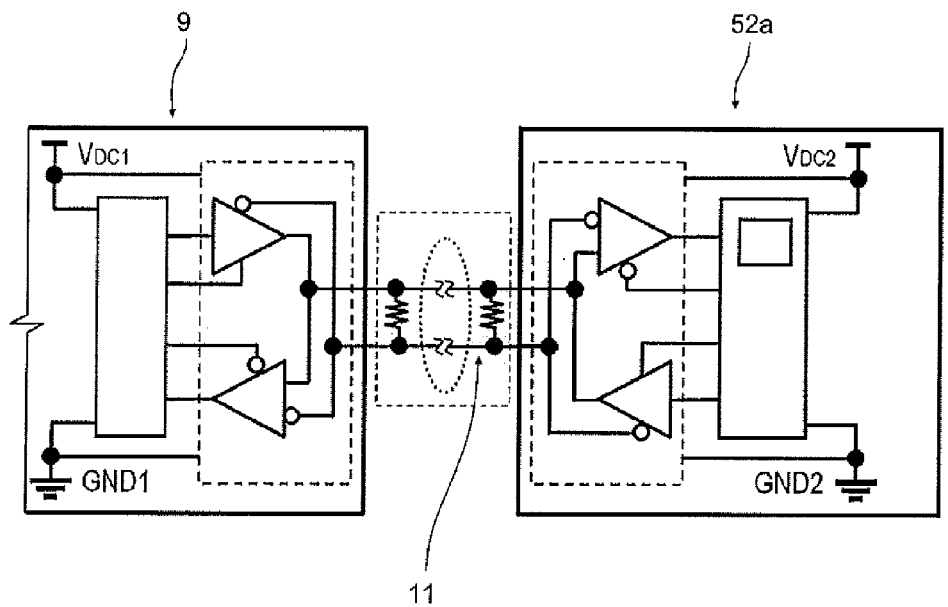
FIG. 3 shows a first embodiment of the communication channel between the diffuser device and the plate.

In an alternative embodiment (FIG. 3), the communication channel is defined by a serial bus. The communication allows the two-way exchange of data, in half duplex mode (one only transmitter active at a time), with a master-slave protocol, with the control unit 8 in the role of master and the processor 52 in the role of slave. From the physical point of view, the data reception module 9 and the transmission module 52a are defined by a transceiver (transmitter and receiver), in turn connected by cable 11.

Preferably, the transceivers are equipped with a termination resistor on each of the two sides of the communication channel. On the side of the diffuser device 1, and of its control unit 8, there is both a transmitter and a receiver.

The above-mentioned transmitter sends on the cable 11 the data to be transmitted which it receives from the control unit 8 (together with a transmission enabling signal).

The above-mentioned receiver provides to the control unit 8 data read from the above-mentioned cable 11 (after receiving the transmission enabling signal provided by the control unit 8).

Similarly, on the side of the processor 52 it is possible to identify both the transmitter and the receiver.

Preferably, the control unit 8 is programmed for calculating a quantity of the liquid solution "L" to be introduced into the room for nebulising as a function of the signal representing identification data of the room "R" sent by the plate 50.

In order to check that this quantity is correct, the diffuser device 1 comprises sensors means 12 associated with the tank 2 and with the control unit 8 and configured to measure a quantity correlated with the quantity of liquid solution "L" dispensed from the nebulising means 3.

The sensor means are also configured for sending a signal representing the quantity to the control unit 8.

In turn, the control unit 8 is configured for calculating a threshold value of the quantity of liquid solution "L" to be dispensed as a function of the signal representing the identification data of the room "R" received from the plate 50 and for comparing the threshold value with the quantity of liquid solution "L" dispensed.

Moreover, the control unit 8 is configured to interrupt the nebulising by the nebulising means 3 (and thus the action of the turbine 4) when the quantity of liquid solution "L" dispensed equals or exceeds the threshold value.

Preferably, the sensor means 12 comprise at least one weight sensor 13 associated with the tank 2.

Thus, the control unit 8 is configured for calculating a variation of the quantity of liquid solution "L" in the tank 2 as a function of a variation of the weight of the tank 2.

More in detail, the tank 2 is positioned in a housing 14 made in a structure 1*a* of the diffuser device 1.

At the base of the housing 14 there is the weight sensor 13, the output signals of which are connected with the control unit 8 so as to be read, determining the current weight of the tank 2 and, consequently, the amount of sanitising solution instantaneously present in the tank 2.

Due to its ease of use and low cost, the weight sensor 13 adopted in the preferred embodiment is of the FSR (Force Sensitive Resistor) type. Other types of weight sensors (e.g. load cell) may be considered, such as, for example, ultrasound or capacitive volumetric sensors.

In this circuit the resistance of the "RFORCE" sensor is represented by the variable resistance, connected to the first input of the operational amplifier. At the second input of the above-mentioned amplifier there is a reference voltage "VREF" applied by a divider. An output of the above-mentioned amplifier is backfed to the input by the feedback resistance (RFDBK) and a filter capacity. The value of the output voltage is given by the following formula:

$$VOUT=VREF\times(1+(RFDBK/RFORCE))$$

An analogue-digital converter makes it possible to read the outfeed voltage value VOUT and correlate it with the weight of the tank 2.

FIG. 6 illustrates the trend of the function VOUT=VOUT (Weight) with the variation of the parameters VREF and RFDBK which determine the sensitivity (slope) and the capacity of the sensor.

FIG. 6 shows the trend of the function VOUT=VOUT (Weight), that is, how the output signal VOUT varies with the variation of the independent Weight variable. The diagram illustrates four parametric curves varying the parameters VREF and RFDBK: the two curves show the trend of the function when VREF corresponds to 1V and RFDBK changes from 30 kΩ to 60 kΩ.

The other two curves show the trend of the function when VREF corresponds to 2V and RFDBK changes from 30 kΩ to 60 kΩ.

By comparing the two pairs of curves it may be noted that VREF determines the minimum weight that the sensor is capable of measuring.

However, by fixing, for example, VREF=2V it may be noted that RFDBK determines the inclination of the curve.

It is evident from the diagram that by varying the two parameters VREF and RFDBK it is possible to vary the capacity and the sensitivity of the sensor, thereby adapting it to the different requirements of the weight sensors 13.

Preferably, also, the nebulising means 3 comprise means 15 for adjusting the flow rate of the nebulised liquid solution "L", also associated with the control unit 8.

The control unit 8 is programmed for sending to the adjustment unit 15 a signal representing the flow rate of liquid solution "L" to be nebulised as a function of the consumption of liquid solution "L" in the tank 2 measured by the sensor means 12.

More specifically, at the start of the treatment the control unit 8 acquires the weight of the tank 2, assuming that the latter is the container in use, and the data of the room "R" to be treated using the plate 50. Knowing the type of room to be processed, for example, in the hospital context, patients ward or operating room, and the volume to be treated, or, more generally, the treatment to be performed, the control unit 8 (that is, the microprocessor) can determine the quantity of sanitising solution to be dispensed and the time necessary. After checking that the tank 2 contains a total quantity of sanitising liquid solution "L" sufficient to complete the dispensing, the control unit 8 starts the treatment activating the turbine 4 of the nebulising means 3 the pump 5, with the average flow rate necessary to complete the treatment in the calculated time. At predetermined intervals of time, the control unit 8, measuring the quantity of solution dispensed in the interval of time and comparing a deviation of the curve of actual consumption (quantity dispensed divided by the time) with the calculated theoretical consumption, determines the correction which must be made to the flow rate of the pump 5 so that the actual flow rate is aligned with the theoretical flow rate.

Advantageously, the pump 5 also allows faults in the system for feeding the nebulising means 3 to be detected. In effect, the control unit 8 by operating together with the sensor means 12 of a quantity correlated with the quantity of liquid solution "L" dispensed, can also check that the consumption of liquid solution "L" is consistent with the flow rate of the pump 5. The nebulising can be interrupted and an error message displayed and recorded, if consumption is greater or less than the set one.

The control unit 8 is also programmed to check (at preset time intervals) that the connection with the plate 50 is enabled, to guarantee that the sanitising is being performed in the preset room and that the diffuser system has not been moved to another room.

The end of the treatment (that is, of the nebulising) will be determined by the reaching the dispensing of the quantity of solution provided, favouring this parameter with respect to time of the treatment.

In other words, if the threshold value of sanitising liquid solution "L" dispensed is reached before a preset duration of the planned treatment, the control unit 8 still sends to the nebulising means a signal representing an interruption of the treatment, stopping it.

In the preferred embodiment, the diffuser device 1 comprises two tanks 2.

In the same way, the diffuser device 1 comprises two weight sensors 13, each associated with a respective tank 2.

Checking that one of the two tanks 2 is always completely full, and allowing the nebulising means 3 to select from which tank to draw, the introduction of the two tanks 2 always allows the full use of liquid solution "L" contained in the tank 2 in use, without forcing the user to transfer liquid solution in the field.

Preferably, also, the tanks 2 are removable and can be replaced. To allow the effectiveness of the contents to be checked, the diffuser device 1 comprises recognition means 16 which can be associated with each tank 2 and configured for identifying the liquid solution "L" contained in the tank 2. These recognition means 16 are associated with the control unit 8.

More specifically, the recognition means 16 comprise a reading unit 16a which can be associated with a label 60 applied to the tank 2 for reading one or more identification data of the liquid solution "L" contained in the label 60.

Preferably, also, the label 60 is rewritable. In this regard, the recognition means 16 also comprise a writing module 16b designed for modifying the identification data of the liquid solution "L" as a function of the consumption of the liquid solution measured by the sensor means 12. These recognition means 16 operate on both the tanks 2.

Thus, each tank 2 is equipped with a relative electronic label 60, containing all the production data of the respective sanitising solution (manufacturer, type of sanitising fluid, date and place of production, expiry date, etc) in addition to the weight of the above-mentioned solution contained therein.

These labels 60 are irremovably attached to the above-mentioned tank 2 and contain readable and writable information.

Preferably, the labels 60 are configured to communicate with the recognition means 16 using two-way wireless and short-range channels.

The electronic labels 60 contemplated in the preferred embodiment are RFID (Radio Frequency IDentification) TAGS.

Other embodiments which are able to contain readable and writable information, non-removable from the tanks 2, that is to say, that attempts to remove cause permanent damage, and which are able to communicate on two-way channels (read and write) with a control card, can be considered.

Preferably, the memory (non-volatile) of the electronic label 60 records (preferably in a coded manner) not only the identification data of the above-mentioned solution, but also the weight of the tank 2 from which, by subtracting the tare weight of the container, it is possible to obtain the weight of the sanitising solution available in the above-mentioned tank 2. The previous data are recorded in the above-mentioned memory, together with a redundancy code, to protect the integrity of the information recorded.

Preferably, the diffuser device 1 also comprises a container 17 of a liquid substance "F", having a predetermined fragrance.

The container 17 is placed in fluid connection with the nebulising means 3.

The control unit 8 is programmed for drawing out the liquid substance "F" from the container 17 and nebulising it in the room "R" after receiving, from the sensor means 2, a signal indicating that the threshold value of the quantity of liquid solution "L" to be dispensed has been exceeded.

Preferably, the nebulising means 3 comprise a solenoid valve 18 with at least two (preferably three) paths having a plurality of inlets 18a, associated with the tank 2 (or the tanks 2) and the container 17.

The control unit 8 is configured for opening the passage of one of the inlets towards a single outlet 18b as a function of the signal received from the control unit 8.

Thus, upon the positive completion of a sanitising treatment (that is, of the nebulising), the control unit 8 (that is, the microprocessor) of the diffuser commands a dispensing of the liquid substance "F" and, therefore, the nebulising of the respective fragrance for a time needed by the user to make an olfactory check of the positive completion of the sanitising of the room.

Preferably, the control unit 8 is programmed for measuring a predetermined interval of time between the end of nebulising and the dispensing of the liquid substance "F" so as to allow the complete removal of the bacteria by the sanitising liquid solution "L" nebulised during the treatment.

More specifically, the solenoid valve 18 receives the sanitising liquid solution "L" from the tanks 2 through the pipes, respectively, or the liquid substance "F" (that is, the fragrance) from the container 17. Under the control of the signals generated by the control unit 8, the solenoid valve is controlled in such a way as to allow the flow of only one of the liquids, directing it to the turbine 4 of the nebulising means 3. Alternatively, however, other solutions for selecting the liquid to be nebulised, different from that described in this preferred embodiment, may be considered.

It should be noted that, similarly to the tanks 2, a sensor 19, which is able to determine the weight of the fragrance present in the container 17, is installed at the base of the housing of the container 17. The above-mentioned weight sensor 19 is connected to the control unit 8 of the diffuser device 1, by an interface circuit, similar to that adopted for determining the weight of the sanitising solution. The control unit 8 is thus able to automatically determine the quantity of liquid substance "F" (that is, fragrance) dispensed at the end of the treatment, as well as the consumption of the fragrance.

It should be noted that the diffuser device 1 comprises a memory 20 (non-volatile and removable) associated with the control unit 8 and designed to receive from it periodically, during or at the end of each nebulising, a plurality of data correlated with:

- the room treated and/or
- the quantity of liquid solution "L" nebulised and/or
- the quantity of liquid solution "L" remaining in the tank 2 and/or
- the date and time of nebulising and/or
- the duration of the nebulising.

In that way, as well as the sequence of treatments performed in each room "R", it is possible to trace in a continuous and/or complete manner the sequence of treatments performed by the diffuser device 1.

It should be noted that the diffuser device 1 may be powered both by a battery and by connection to the electricity network.

Preferably, in this regard, the diffuser device 1 is equipped with an AC/DC power supply module 21 configured for receiving the AC voltage (by a cable connected to the wall-mounted power supply socket).

The DC voltage, converted from the AC voltage and reduced in voltage, is supplied to the control unit 8 by means of an internal DC power supply cable. The other functional modules that require a DC supply voltage receive it from the above-mentioned control unit. The functional modules that require an AC supply voltage receive it directly from the internal power supply cable.

With reference to the entire system 100 for disinfecting rooms and surfaces, according to the invention, it comprises at least one control device 80 which can be used by an operator and connectable to the diffuser device 1.

The control device 80 comprises an interface module 81 which can be used by the operator and at least one processing module 82 connectable to the memory 20 of the diffuser device 1 for picking up a plurality of data correlated with each nebulising.

Similarly, the control device 80 is connectable to the plate 50.

More specifically, the processing module 82 can be connected to the processor 52 of the plate 50 to enable the operator to enter the identification data of the room "R" to be treated.

Moreover, the control device 80 is connectable to the memory 51 of the plate 50 to pick up the data relating to the treatments performed in the respective room "R" thereby allowing the quality and the frequency of treatments to be traced and kept under control.

Thus, the control device 80 is configured for allowing an operator to communicate in a two-way fashion both with the processor 52 of the above-mentioned electronic plate 50 and with the control unit 8 (or microprocessor **8*a*) of the above-mentioned diffuser device 1**.

More specifically, the control device 80 is programmed for allowing an operator to initialise the memory 51 (non-volatile) of the processor 51 of the above-mentioned plate 50 with all the data relative to the room "R" in which it has been installed.

Moreover, the control device 80 is configured for collecting the data recorded in the memory 20 (non-volatile) of the above-mentioned microprocessor **8*a* of the diffuser device 1**.

Preferably, the control device 80 will be made available only to authorised operators.

In this regard, the processing module 82 of the control device 80 is programmed to set up an identification procedure. More specifically, the module 82 is programmed for requesting identification data from the operator and comparing it with corresponding data held in the memory of the plate 51 or of the diffuser device 20, allowing access only if the data provided by the operator corresponds with data in the respective memory 20, 51.

Preferably, however, the system 100 is configured for transferring the data in coded form and to make the data readable only when the above-mentioned control device 80 is connected to an apparatus outside the system, such as a personal computer, where the data may be analysed, printed and archived.

Thus, the system 100 according to this invention provides a method for sanitising rooms and surfaces which is highly efficient and traceable at every step.

The method comprises providing a plate 50, as described above, inside a room to be sanitised.

There is also a step of setting up identification data of the room, preferably using the control device 80.

In the preferred embodiment, a plurality of plates 50 is positioned in a corresponding plurality of rooms "R" to be sanitised and, preferably, each of them is set up with the identification data of the respective room.

Then, at the time of sanitising, a diffuser device 1 is located inside the room "R" to be treated.

The diffuser device 1 is placed in communication with the plate 50 for detecting the above-mentioned identification data.

Preferably, the control unit 8 of the diffuser device 1 is put in communication (through the two-way channel described above) with the processor 52 of the plate 50.

More specifically, the communication is maintained constantly for the entire duration of the treatment to guarantee that the above-mentioned device is not removed from the room during the sanitising.

Thus, a sanitising liquid solution "L" is nebulised in the room for an interval of time and with a flow rate which are both a function of the identification data detected.

Preferably, during the nebulising there is a step of controlling the consumption of the liquid solution "L" by means of a comparison between the consumption measured and an estimated value as a function of the identification data.

Preferably, the consumption is measured in relation to the variation of weight of the tank 2 of liquid solution "L", more preferably by the use of sensor means 12 described previously.

When a threshold value of liquid solution dispensed (that is, consumed) is reached or exceeded and/or at the end of the estimated time interval, the nebulising is interrupted.

Preferably, the quantity of liquid solution "L" is a predominant parameter relative to the duration of the treatment, as the latter is subordinate to the reaching of the above-mentioned threshold value.

During the nebulising there is a further step of controlling the connection between the diffuser device 1 and the plate 50, to guarantee that the sanitising occurs in the selected room, that is to say, that the above-mentioned system is not moved to another room.

After nebulising the liquid solution "L" is completed, the method preferably comprises emission into the environment of a predetermined fragrance, preferably drawn out from a container 17 such as that described above.

Preferably, there is a predetermined period of time between the end of the nebulising and the dispensing of the fragrance, more preferably fixed on the basis of operating protocols with the structure involved and in compliance with the national laws and regulations.

Advantageously, this fragrance allows the operator to immediately determine the positive conclusion of the treatment, by noting the scent of the fragrance present in the air of the room.

Thus, the diffuser device 1 allows a method to be implemented for the sensorial detection (olfactory) of a correct and positive sanitising of the room, without the need to export the data from the diffuser device 1 or from the plate 50, with a considerable saving of time.

The invention achieves the proposed aims and brings significant advantages.

In effect, the use of a diffuser device interfaced with an electronic plate provided with all the identification data of the room allows an automatic and secure solution to be obtained for the traceability which allows the user to check, and therefore demonstrate, that clearly identified rooms have been sanitised with precise dates, methods and times.

It should be noted that the presence of the sensor means and of the control unit especially programmed can guarantee to the user that exactly the quantity of solution required to sanitise a given room has been dispensed.

Moreover, the use of a rewritable electronic label guarantees the identity and the authenticity of the solution used, avoiding tampering or falsifying of the solution.

Moreover, the preparation of a container with a liquid substance, having a predetermined fragrance, allows a method to be implemented which allows the user to check the disinfection with the sensors provided.

The invention claimed is:

1. A diffuser device for a system for disinfection of spaces and surfaces in a room to be treated, wherein the room to be treated includes a plate containing a plurality of identification data of the room to be treated, the diffuser device comprising:
a tank containing a liquid solution,
a nebulizer in fluid connection with the tank for drawing out the liquid solution from the tank and nebulizing by spraying the liquid solution into the room to be treated for disinfecting the room to be treated,
a control unit associated with the nebulizer and with the plate, the control unit programmed such that it receives from the plate a signal representing identification data of the room to be treated, the control unit programmed such that it controls the nebulizer as a function of the signal to disinfect the room to be treated in an automatic manner;
wherein the control unit is programmed such that it communicates with the plate periodically or continuously during operation of the nebulizer to prevent the diffuser device from being moved from the room to be treated while the disinfecting in the room to be treated is in progress;
wherein the control unit is programmed such that it commands stopping of the nebulizer following a communication failure with the plate to prevent the diffuser device from being moved from the room to be treated while the disinfecting in the room to be treated is in progress.

2. The diffuser device according to claim 1, wherein the control unit comprises a data reception module operatively connectable to the plate for receiving the signal.

3. The diffuser device according to claim 1, wherein the control unit is programmed for calculating a quantity of the liquid solution to be introduced into the room to be treated for nebulizing as a function of the signal.

4. The diffuser device according to claim 1, wherein the diffuser device comprises a sensor associated with the tank and the control unit for measuring a quantity correlated with a quantity of liquid solution dispensed by the nebulizer and for sending a quantity signal representing the quantity to the control unit; the control unit being programmed to calculate a threshold value of the quantity of liquid solution to be dispensed as a function of the signal representing identification data of the room to be treated, for comparing the threshold value with the quantity of liquid solution dispensed and for interrupting the nebulizing by the nebulizer when the quantity of liquid solution dispensed exceeds the threshold value.

5. The diffuser device according to claim 4, wherein the sensor comprises a weight sensor associated with the tank; the control unit being programmed for calculating a variation in the quantity of liquid solution in the tank as a function of a variation of weight of the tank.

6. The diffuser device according to claim 4, wherein the nebulizer comprises an adjustment device for adjusting a flow rate of the nebulized liquid solution, the adjustment device associated with the control unit; the control unit being programmed such that it send to the adjustment device a signal representing the flow rate of liquid solution to be nebulized as a function of a consumption of liquid solution in the tank measured by the sensor.

7. The diffuser device according to claim 4, and further comprising a container of a liquid substance, having a predetermined fragrance, in fluid connection with the nebulizer; the control unit being programmed such that it controls the nebulizer to draw out the liquid substance from the container and nebulize the liquid substance into the room to be treated after receiving, from the sensor, a signal indicating that the threshold value of the quantity of liquid solution to be dispensed has been exceeded.

8. The diffuser device according to claim 1, wherein the control unit comprises a recognition device associated with the tank for identifying the liquid solution contained in the tank.

9. The diffuser device according to claim 8, wherein the recognition device comprises a reading unit associated with a label applied to the tank for reading from the label, identification data of the liquid solution.

10. The diffuser device according to claim 9, wherein the recognition device also comprises a writing module for modifying the identification data of the liquid solution as a function of consumption of the liquid solution measured by the sensor.

11. The diffuser device according to claim 1, and further comprising a memory associated with the control unit for receiving from the control unit, during or at an end of each nebulizing, a plurality of data correlated with at least one chosen from:
the room treated;
a quantity of liquid solution nebulized;
a quantity of liquid solution remaining in the tank;
a date and time of nebulizing
a duration of the nebulizing.

12. A system for the disinfection of spaces and surfaces, and further comprising:
the diffuser device according to claim 1;
the plate, wherein the plate includes a memory containing the plurality of identification data of the room to be treated, the plate positioned in the room to be treated spatially removed from the diffuser device.

13. The system according to claim 12, wherein the plate comprises a processor associated with the memory and programmable by an operator for entering the identification data of the room to be treated.

14. The system according to claim 13, wherein the control unit comprises a data reception module operatively connectable to the plate for receiving the signal; wherein the processor includes a transmission module connectable to the data reception module for sending to the diffuser device the identification data of the room to be treated.

15. The system according to claim 14, wherein the transmission module is arranged for communicating with the data reception module periodically or continuously during the nebulizing so as to check during the treatment the presence of the diffuser device in the room to be treated.

16. The system according to claim 13, and further comprising a control device which can be used by an operator and connectable to the plate; the control device comprising an interface module which can be used by the operator and at least one processing module connectable to the processor of the plate for allowing the operator to enter the identification data of the room to be treated.

17. The system according to claim 12, and further comprising a control device which can be used by an operator and connectable to the diffuser device; the control device comprising an interface module which can be used by the operator and at least one processing module connectable to the memory of the diffuser device for picking up a plurality of data correlated with each nebulizing.

18. A method for the disinfection of spaces and surfaces, comprising:
providing a plate in a room to be treated, the plate including a memory containing a plurality of identification data of the room;
providing a diffuser device equipped with a tank containing a liquid solution and a nebulizer associated with the tank for drawing out the liquid solution from the tank and spraying the liquid solution into the room to be treated for disinfecting the room to be treated;
providing the diffuser device with a control unit associated with the nebulizer and with the plate, the control unit programmed such that it receives from the plate a signal representing identification data of the room to be treated, the control unit programmed such that it controls the nebulizer as a function of the signal to disinfect the room to be treated in an automatic manner;
communicating the identification data of the room to be treated from the plate to the control unit;
calculating, by the diffuser device, a predetermined duration of treatment and a predetermined quantity of liquid solution to be introduced into the room to be treated;
nebulizing the predetermined quantity of liquid solution for an interval of time corresponding with the predetermined duration;
providing that the control unit communicates with the plate periodically or continuously during operation of the nebulizer to prevent the diffuser device from being moved from the room to be treated while the disinfecting in the room to be treated is in progress;
providing that the control unit commands stopping of the nebulizer following a communication failure with the plate to prevent the diffuser device from being moved from the room to be treated while the disinfecting in the room to be treated is in progress.

19. The method according to claim 18, and further comprising controlling a consumption of liquid solution "L", using the control unit of the diffuser device, by comparing a measured consumption and a value estimated as a function of the identification data.

20. The method according to claim 19, and further comprising measuring the consumption of liquid solution by controlling a variation in weight of the tank of liquid solution during the nebulizing.

21. The method according to claim 18, and further comprising, at an end of nebulizing the liquid solution, nebulizing a liquid substance having a predetermined fragrance, different from that of the liquid solution.

22. The method according to claim 21, wherein the step of nebulizing a liquid substance having a predetermined fragrance, different from that of the liquid solution is performed at an end of a predetermined interval of time after the end of the nebulizing of the liquid solution.

23. The method according to claim 21, wherein the step of nebulizing a liquid substance having a predetermined fragrance is performed after reaching or exceeding a threshold value of the quantity of liquid solution dispensed.

24. A diffuser device for a system for disinfection of spaces and surfaces in a room to be treated, wherein the room to be treated includes a plate containing a plurality of identification data of the room to be treated, the diffuser device comprising:
a tank containing a liquid solution,
a nebulizer in fluid connection with the tank for drawing out the liquid solution from the tank and spraying the liquid solution into the room to be treated for disinfecting the room to be treated,
a control unit associated with the nebulizer and with the plate, the control unit programmed such that it receives from the plate a signal representing identification data of the room to be treated, the control unit programmed such that it controls the nebulizer as a function of the signal to disinfect the room to be treated in an automatic manner;
wherein the control unit comprises a recognition device associated with the tank for identifying the liquid solution contained in the tank;
wherein the recognition device comprises a reading unit associated with a label applied to the tank for reading from the label, identification data of the liquid solution;

wherein the recognition device also comprises a writing module for modifying the identification data of the liquid solution as a function of consumption of the liquid solution measured by the sensor.

* * * * *